US00PP15773P2

(12) United States Plant Patent
Zary

(10) Patent No.: US PP15,773 P2
(45) Date of Patent: May 17, 2005

(54) HYBRID TEA ROSE NAMED 'JACFRENS'

(50) Latin Name: *Rosa hybrida*
Varietal Denomination: JACfrens

(75) Inventor: Keith W. Zary, Somis, CA (US)

(73) Assignee: Jackson & Perkins Wholesale, Inc., Medford, OH (US)

( * ) Notice: Subject to any disclaimer, the term of this patent is extended or adjusted under 35 U.S.C. 154(b) by 0 days.

(21) Appl. No.: 10/848,728

(22) Filed: May 18, 2004

(51) Int. Cl.[7] ..... A01H 5/00
(52) U.S. Cl. ..... Plt./132
(58) Field of Search ..... Plt./132, 130, 134

*Primary Examiner*—Anne Marie Grunberg
*Assistant Examiner*—June Hwu
(74) *Attorney, Agent, or Firm*—Klarquist Sparkman LLP

(57) ABSTRACT

Hybrid tea rose plant having large, bright, early yellow flower changing to a blend as it ages; sweet fragrance; dark, glossy foliage; resistance to powdery mildew and rust; and ability to grow vigorously on its own roots.

1 Drawing Sheet

Genus and species: *Rosa hybrida.*
Variety denomination: 'JACfrens'.

ORIGIN OF THE INVENTION

The present invention relates to a new and distinct variety of a hybrid tea rose plant named 'JACfrens' which was originated by me by crossing the variety 'KElbian', U.S. Plant Pat. No. 8,476, with the variety 'JACjel', U.S. Plant Pat. No. 4,438.

BACKGROUND OF THE INVENTION

The primary objective of this breeding was to produce a new rose variety having the fragrance and good disease resistance of the female parent combined with the large, bright yellow flower of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large, bright early flower changing to blend as it ages.
2. Sweet fragrance.
3. Dark, glossy foliage.
4. Resistance to powdery mildew and rust.
5. Ability to grow vigorously on its own roots.

Asexual reproduction of this new variety by cuttings, as performed at Wasco, Calif., shows that the foregoing and all other characteristics and distinctions come true to form and are established and transmitted through succeeding propagations.

COMPARISON WITH PARENTS

As compared to the female parent 'KElbain', 'JACfrens' differs in flower color being brighter yellow, and having less color change as it ages. As compared to the male parent, 'JACfrens' differs in having much more fragrance and having a blend of color in the old flower. 'JACjel' is pure yellow.

COMPARISON WITH SIMILAR VARIETY

A similar variety is 'MEIlvar', U.S. Plant Pat. No. 7,541) which has more petals but less fragrance than 'JACfrens' and has pure yellow flowers without any blush on petals.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'KElbian' (French Perfume), U.S. Plant Pat. No. 8,476.

*Pollen parent.*—'JACjel' (Sunbright), U.S. Plant Pat. No. 4,438.

FLOWER

Observations made of plants commencing at two years of age, grown from bare roots in a garden environment at Somis, Calif., from January to October 2003.

Blooming habit: Continuous.

Bud:

*Size.*—About 4 cm long and 2.5 cm in diameter when the petals start to unfurl.

*Form.*—The bud form is long, pointed ovoid.

*Color.*—When sepals first divide, bud color is Yellow Group 4B with streaks of Red Group 53D. When half blown, the upper sides of the petals are Yellow Group 4B with the outer row of petals tipped in Red Group 53D along margin; and the lower sides of the petals are Yellow Group 4B with the outer row tipped in Red Group 53D.

*Sepals.*—Color: Upper surface: Green Group 138B but often, especially in bright sunlight overcast with Greyed-Purple Group 183D. Lower surface: Green Group 138A. Length: 30–35 mm. Width: 8–10 mm. Shape: Subulate. Surface texture: Upper surface: Hoary. Lower surface: Scabridulous. There are three lightly appendages sepals. There are two unappendaged sepals with hairy edges.

*Receptacle.*—Color: Green Group 138B. Shape: Funnel. Size: Medium, about 6 mm long×8 mm wide. Surface: Smooth.

*Peduncle.*—Length: Long, averaging about 11–13 cm. Surface: Rough, prickly, glandular. Color: Green Group 148B. Strength: Stiff, erect.

Bloom:

*Size.*—Large. Average open diameter is about 12–13 cm.

*Borne.*—Singly.

*Stems.*—Strength: Strong. Average length is about 30–45 cm with a diameter of 6–7 mm.

*Form.*—When first open: High centered. Permanence: Flattens, all petal edges curl slightly.

*Petalage.*—Number of petals under normal conditions: 35–40.

*Color.*—The upper sides of the petals are Yellow Group 4B with the outer row tipped in Red Group 53B. The reverse sides of the petals are Yellow Group 4B with outer row tipped in Red Group 53B. The base of each petal has a deep yellow color spot of Yellow Group 5A, about 4 mm by 4 mm in size. The major color on the upper side is Yellow Group 4B.

*Variegations.*—None.

*Discoloration.*—The general tonality at the end of the first day: No change. At the end of the third day: No change. Further aging: By day 5, there becomes a blush of Red Group 53B on petal tips.

*Fragrance.*—Strong, sweet fruity.

Petals:

*Texture.*—Thick.

*Shape.*—Round to slightly deltoid.

*Surface.*—Smooth.

*Margin.*—Smooth and entire. Apex shape: Rounded. Base shape: Rounded.

*Form.*—Tips slightly recurved.

*Arrangement.*—Imbricated.

*Petaloids.*—Number: 4–7. Color: Yellow Group 4B. Size: 7–9 mm long, 3–5 mm wide.

*Persistence.*—Petals drop off cleanly before drying.

*Lastingness.*—On the plant: Long (about 6–7 days). As a cut flower: Long (about 8–9 days).

Reproductive parts:

*Stamens.*—Number: 60–70. Length: 11–12 mm. Anthers: Length: 3 mm. Color: Yellow-Orange Group 16B. Filaments: Color: Yellow-Orange Group 16C. Length: 8–9 mm. Pollen: Color: Yellow-Orange Group 22C.

*Pistils.*—Number: 40–50. Length: 7–8 mm. Styles: Color: Red Group 45D. Length: 6–7 mm. Stigmas: Color: Yellow-Orange Group 21D. Length: 1 mm.

*Hips.*—None observed.

PLANT

*Form.*—Bush.

*Growth.*—Vigorous.

*Age at maturity.*—Two years.

*Mature plant.*—Height: 180 cm. Width: 120 cm.

*Rootstock.*—Own root.

Foliage: Number of leaflets on normal mid-stem leaves: 5–7.

*Size.*—Large. About 15 cm long×10 cm wide.

*Quantity.*—Abundant.

*Color.*—New foliage: Upper side: Greyed-Red Group 178A. Lower side: Greyed-Red Group 178A. Old foliage: Upper side: Green Group 136A. Lower side: Green Group 137D.

Leaflets:

*Size.*—About 4.5 cm long×3.5 cm wide.

*Shape.*—Pointed oval.

*Base shape.*—Rounded.

*Apex shape.*—Acuminate.

*Texture.*—Leathery.

*Edge.*—Serrated.

*Serrations.*—Single.

*Petiole.*—Color: Yellow-Green Group 147C.

*Petiole rachis.*—Color: Yellow-Green Group 148B. Underside: Rough with prickles.

*Auricle shape, if present.*—None.

*Stipules.*—Shape: Adnate. Length: 16 mm. Smooth, edged in glands.

*Disease resistance.*—Resistance to mildew and rust, susceptible to blackspot under normal growing conditions.

*Pest resistance.*—Not observed.

*Vein color.*—Same as leaf.

*Venation pattern.*—Reticulate.

Wood:

*New wood.*—Color: Greyed-Red Group 178A. Bark: Smooth.

*Old wood.*—Color: Green Group 138B. Bark: Smooth.

Prickles:

*Quantity.*—On main canes from base: Few. On laterals from main canes: Few.

*Form.*—Straight.

*Length.*—8 mm.

*Color when young.*—Greyed-Purple Group 184B.

*Color when mature.*—Greyed-Green Group 194C.

Small prickles:

*Quantity.*—On main stalks: None. On laterals: Few.

*Color.*—Greyed-Green Group 195D.

*Length.*—1–2 mm.

Winter hardiness: Hardy to Zone 5.

I claim:

1. A new and distinct variety of rose plant of the hybrid tea class, substantially as herein shown and described, characterized particularly by its large, bright, early yellow flower changing to a blend as it ages; sweet fragrance; dark, glossy foliage; resistance to powdery mildew and rust; and ability to grow vigorously on its own roots.

* * * * *

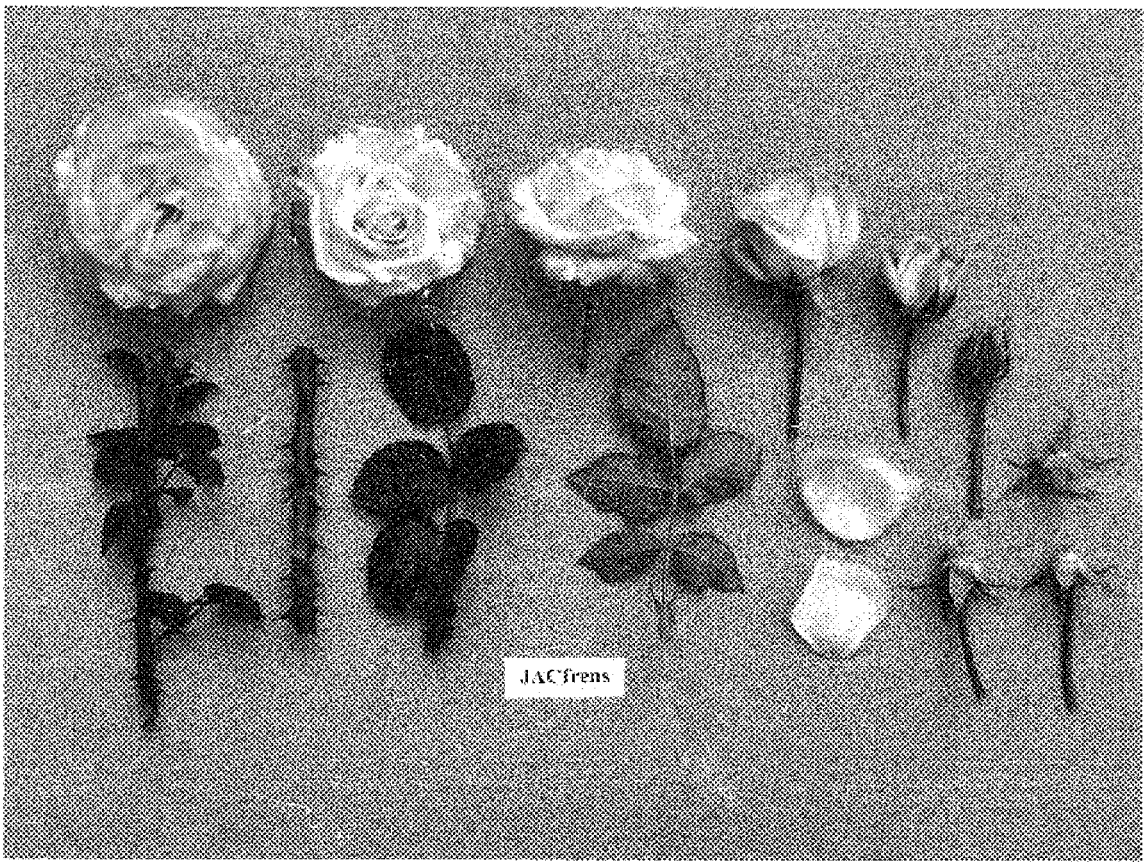
JAC'frens

UNITED STATES PATENT AND TRADEMARK OFFICE

CERTIFICATE OF CORRECTION

PATENT NO. : PP 15,773 P2
DATED : May 17, 2005
INVENTOR(S) : Keith W. Zary

It is certified that error appears in the above-identified patent and that said Letters Patent is hereby corrected as shown below:

Title page,
Item [73], Assignee, should read -- Jackson & Perkins Wholesale, Inc., Medford, OR (US) --.

Signed and Sealed this

Eighth Day of November, 2005

JON W. DUDAS
*Director of the United States Patent and Trademark Office*